United States Patent [19]

Boudakian et al.

[11] Patent Number: 4,999,434

[45] Date of Patent: Mar. 12, 1991

[54] PROCESS FOR LOW CHLORIDE 1,2,4-TRIAZOL-5-ONE

[75] Inventors: Max M. Boudakian, Pittsford; Delmer A. Fidler, Rochester, both of N.Y.

[73] Assignee: Olin Corporation, Cheshire, Conn.

[21] Appl. No.: 101,465

[22] Filed: Sep. 28, 1987

[51] Int. Cl.$^5$ .......................................... C07D 249/08
[52] U.S. Cl. .................................................. 548/263.2
[58] Field of Search ........................................ 548/263

[56] References Cited

U.S. PATENT DOCUMENTS

| | | | |
|---|---|---|---|
| 2,763,661 | 9/1956 | Grundmann et al. | 260/308 |
| 3,890,342 | 6/1975 | Krenzer | 548/263 |
| 3,922,162 | 11/1975 | Krenzer | 548/263 |
| 4,467,098 | 8/1984 | Koch et al. | 548/263 |
| 4,482,738 | 11/1984 | Rothgery | 564/37 |

OTHER PUBLICATIONS

Chem. Abst. 54; 22602: *Ann. Chim.,* (Rome) 49, 1649–67 (1959), "Reactions Between Organic Nitrogen Compounds and Ethyl Orthoformates. I. Hydrazides and Derivatives".
*Chemische Berichte,* vol. 98–II, "Synthesen und Reaktionen von 4-Amino-1.2.4-Triazolonen-(5)", pp. 3025–3033, 1965.
*Chemische Berichte,* vol. 98–II, "Die Umsetzung Alkyl-substituierter Semicarbazide Mit Orthoameisensaure--Triathylester", pp. 3034–3039, 1965.
Chem. Abst. 62; 14437: *Ann. Chem.* 682, pp. 123–135, (1965) (Germany), "1,2,4-Triazol-5-ones. V. Effect of Substituents on the Rate of Hydrolysis in Half-Concentrated Sulfuric Acid".
Chem. Abst. 65; 705: *Khim. Geterotsikl. Soedin., Akad. Nauk Latv. SSR,* 1966 (1), pp. 110–116 (Russian), "$\Delta^5$-1,2,4-Triazolin-3-one and its Nitro and Amino Derivatives".
*Chemische Berichte,* vol. 100–II, "Die Bromierung von 1.2.4-Triazolen", pp. 2250–2257 (1967).
Chem. Abst. 100; 34468: Ann. Univ. Mariae Curie-Sklodowska, Sect. AA: Chem. 1979 (Publ. 1982), 34, pp. 163–168 (Polish), "Triformylaminomethane. III. Reaction with Thiosemicarbazide, Semicarbazide, and Aminoguanidine".
*Chemical Reviews,* "Formylating Agents", (G. A. Olah et al), American Chemical Society, vol. 87, No. 4, Aug. 1987, pp. 671–686.

*Primary Examiner*—Olik Chaudhuri
*Assistant Examiner*—George R. Fourson
*Attorney, Agent, or Firm*—James B. Haglind; Paul Weinstein

[57] ABSTRACT

A process for producing 1,2,4-triazol-5-one comprises reacting a semicarbazide compound with a formic acid compound formylating agent in the presence of a catalytic amount of a sulfur-oxygen containing acid.

The process is able to produce 1,2,4-triazol-5-one from semicarbazide hydrochloride having significantly lower concentrations of chloride ion, which is advantageous, for example, in the production of 3-nitro-1,2,4-triazol-5-one as an explosive used in castable explosive compositions.

10 Claims, No Drawings

PROCESS FOR LOW CHLORIDE 1,2,4-TRIAZOL-5-ONE

This invention relates to a process for the production of triazolone compounds. More particularly, the invention relates to a process for the production of 1,2,4-triazol-5-one from semicarbazide compounds.

1,2,4-Triazol-5-one (or its tautomeric form; 5-hydroxy-1H-1,2,4-triazole) is a known compound useful as an intermediate in the production of explosives and in the synthesis of dyestuffs.

The preparation of 1,2,4-triazol-5-one has been reported by a number of investigators. C. Runti et al [Ann. Chim. (Rome) 49, 1649–1667, 1959: Chem. Abstracts 54,22602 k (1960)]refluxed semicarbazide.HCl with ethylorthoformate for one hour, the reaction mixture cooled, filtered, and crystallized from ethanol to give 1,2,4-triazol-5-one.

C. F. Kroeger et al prepared 4-amino-1,2,4-triazol-5-one by heating carbohydrazide and ethylorthoformate on a water bath. The amino derivative was deaminated by treatment with $NaNO_2$ in HCl and neutralized with NaOH [Chem. Ber. 98 (9) 3025–3033 (1965); Chem. Abstracts 63,16339 g (1965)].

1,2,4-Triazol-5-one was prepared by G. I. Chipen et al by several methods including the reaction of formic acid with acetone semicarbazone and with semicarbazide.HCl, the latter method being considered optimal. Semicarbazide.HCl and 85 percent formic acid were boiled for 8 hours and kept for 12 hours at 0° C. to prepare of 1,2,4-triazol-5-one. [Khim. Geterotsikl. Soed. 2 (1) 110–116 (1966); Chem. Abstracts 65,705 b (1966)].

M. Dobosz prepared 1,2,4-triazol-5-one by the reaction of triformylaminomethane with semicarbazide or its hydrochloride as reported in Ann. Univ. Mariae Curie-Sklodowska, Sect. AA: Chem. 34, 163 (1979), Chem. Abstracts 100, 34468, (1984).

The preparations recorded in the prior art give 1,2,4-triazol-5-one in low yields or where semicarbazide.HCl is a reactant, the product contains high concentrations of chloride ions. In an important application, the triazolone compound is nitrated to produce 3-nitro-1,2,4-triazol-5-one which is used in cast explosive compositions. It is known that the presence of high chloride concentrations in castable explosives stored, for example, in metal casings results in increased corrosion of the casings and increased gas formation.

In addition, 1,2,4-triazol-5-one having high chloride concentrations of chloride ion can undergo undesired chemical reactions. For example, Kroeger et al (Chem. Ber. 100, 2250 (1967)) found that when 3-nitro-1,2,4-triazol-5-one was heated with hydrochloric acid, chlorodenitration resulted and 3-chloro-1,2,4-triazol-5-one was formed in 87 percent yield.

Therefore, there is a need for a process for producing 1,2,4-triazol-5-one having improved yields and having reduced concentrations of impurities such as chlorides.

It is an object of the invention to provide a process for producing 1,2,4-triazol-5-one in improved yields.

Another object of the invention is to provide a process for producing 1,2,4-triazol-5-one having lower amounts of impurities such as chlorides.

A further object of the present invention is to provide 1,2,4-triazol-5-one which is suitable for producing castable explosives having reduced concentrations of impurities.

These and other objects of the invention are accomplished in a process for producing 1,2,4-triazol-5-one by reacting a semicarbazide compound with a formic acid compound formulating agent in the presence of a catalytic amount of a sulfur-oxygen containing acid.

The novel process of the present invention employs as one reactant a semicarbazide compound. Suitable semicarbazide compounds include semicarbazide, semicarbazones, carbohydrazide, and salts thereof. Preferred as the hydrazine reactant is a semicarbazide compound represented by the formula:

$$XNHC(O)NHN(H)_mY \qquad (I)$$

wherein
X represents H or $NH_2$,
Y represents H, =C(R) (R') or $C(NH)NH_2$,
R represents an alkyl group having from 1 to about 6 carbon atoms, or
R' represents an alkyl group having from 1 to about 6 carbon atoms, or taken together R and R' represent the atoms necessary to complete a cyclohexyl group, and
m represents 0 or 1.

Examples of the semicarbazide compounds represented by Formula I include semicarbazide, carbohydrazide, semicarbazones such as acetone semicarbazone, methyl ethyl ketone semicarbazone, methyl isopropyl ketone semicarbazone, cyclohexanone semicarbazone, and salts thereof.

More preferred as a reactant are semicarbazide compounds represented by Formula I in which X represents H or $NH_2$; Y represents H or =C(R)(R') where R and R' are alkyl groups having from 1 to about 3 carbon atoms; and m represents 1. Examples of the more preferred semicarbazide compounds include semicarbazide and its salts such as semicarbazide hydrochloride or semicarbazide mono- or bisulfate, carbohydrazide, and acetone semicarbazone or methyl ethyl ketone semicarbazone.

In the novel process of the present invention, the semicarbazide compound is reacted with a formic acid compound formulating agent which results in the ring-forming or cyclization reaction required to produce the 1,2,4-triazol-5-one.

Suitable formulating agents include those represented by the formula:

$$HCZ \qquad (II)$$

wherein
Z represents $O_2H$, $O_2R''$, $(OR'')_3$, $O_2M$, $ONH_2$, or $(NHCHO)_3$ wherein
R'' represents a lower alkyl group, and
M represents an alkali metal.

Suitable formulating agents represented by Formula II include formic acid, formic acid esters ($O_2R''$) or orthoformic acid esters $(OR'')_3$ having 1 to about 6 carbon atoms, alkali metal formates such as sodium formate or potassium formate, formamide, and triformylaminomethane.

Preferred as formulating agents are formic acid compounds represented by Formula II wherein Z represents $O_2H$, $O_2R''$, or $(OR'')_3$ in which R'' represents a lower alkyl group having from 1 to about 3 carbon atoms. Examples of these preferred embodiments include formic acid, methylorthoformate, and ethyl orthoformate.

The novel process of the present invention employs catalytic amounts of a sulfur-oxygen containing acid i.e., a sulfur-oxygen containing acid or a sulfonating agent. Suitable sulfur-oxygen containing acids include sulfuric acid, oleum, sulfurous acid, perfluorosulfonic acid resins such as those produced commercially and sold under the trademarks "NAFION" by E. I. Du Pont de Nemours & Company, or "FLEMION" by Asahi Glass Company, and alkyl sulfonic acids in which the alkyl group contains from 1 to about 6 carbon atoms and exemplified by methanesulfonic acid, ethanesulfonic acid, 1,2-ethanedisulfonic acid, and pentanesulfonic acid sodium salt.

Preferred as a sulfur-oxygen containing acid are sulfuric acid, oleum, and alkyl sulfonic acids in which the alkyl group contains from 1 to about 3 carbon atoms; with sulfuric acid being more preferred.

The novel process of the present invention employs catalytic amounts of the sulfur-oxygen containing acid which are admixed with the semicarbazide compound and the formulating agent and which enhance the production of 1,2,4-triazol-5-one. Suitable amounts include those, for example, which provide molar ratios of from about 0.05:1 to about 1:1, and preferably from about 0.1:1 to about 0.5:1. The higher concentrations of the sulfur-oxygen containing acid are employed where, for example, sulfuric acid is employed in a reaction mixture in which a sulfate salt of semicarbazide is formed in situ.

To conduct the process of the invention, the semicarbazide compound, the formulating agent and the sulfur-oxygen containing acid as catalyst are heated at temperatures up to about reflux to produce a reaction mixture containing 1,2,4-triazol-5-one. While the reaction is preferably conducted at about atmospheric pressure, superatmospheric pressures may be employed if desired. The reaction mixture is cooled and the product isolated by known procedures. Where formic acid is the formulating agent, an azeotrope with water is formed which is stripped from the reaction mixture before cooling and recovering the 1,2,4-triazol-5-one product. Alternatively, the reaction product can be filtered and the filter cake washed with water.

The efficacy of the sulfur-oxygen containing acid catalyst in the cyclization reaction to produce 1,2,4-triazol-5-one by the process of the present invention is surprising in view of the teachings of Gehlen et al who studied the hydrolysis of 1,2,4-triazol-5-one and substituted derivatives in 51.60 percent $H_2SO_4$ at 130° C. (Ann. Chem. 682, 123-35, 1965; Chem. Abstracts 62,14437 c, 1965). The hydrolysis reaction resulted in a facile ring scission of 1,2,4-triazol-5-one to give hydrazine, carbon dioxide, ammonia, and formic acid, with a reported hydrolysis rate of $20.7 \pm 0.2$ [k $\times$ 102] [hr$^{-1}$] and a half-life time of 3.35 hours.

When semicarbazide (i.e., semicarbazide as a free base) is reacted with a formic acid ester in the presence of the sulfur-oxygen containing acid catalyst by the process of the invention, 1,2,4-triazol-5-one is produced as the sole product. This is significant in view of the known reaction of semicarbazide with a formic acid ester where, in the absence of the sulfur-oxygen containing acid catalyst, hydrazodicarbonamide is produced as reported by C. Kroeger et al in Chem. Ber. 98, 3034 (1965).

The semicarbazide compound employed in the reaction may itself be produced in situ from a hydrazine compound. For example, semicarbazide hydrochloride may be produced by the reaction of hydrazine with urea and hydrogen chloride as described in U.S. Pat. No. 4,482,738, issued Nov. 13, 1984 to E. F. Rothgery, the entire contents being incorporated by reference herein. Where this is the case, isolation of the semicarbazide hydrochloride produced may be unnecessary.

The use of carbohydrazide as the semicarbazide compound produces an amino-substituted 1,2,4-triazol-5-one which is deaminated by known procedures to provide the desired product.

The novel process of the present invention produces 1,2,4-triazol-5-one in increased yields and/or in higher purity than processes of the prior art.

The process is able to use a semicarbazide salt such as semicarbazide hydrochloride and produce 1,2,4-triazol-5-one having significantly lower concentrations of chloride ion which are advantageous, for example, in the production of 3-nitro-1,2,4-triazol-5-one as an explosive used in castable explosive compositions.

The following examples further illustrate the novel process of the invention without any intention of being limited thereby. All parts and percentages are by weight unless otherwise specified.

EXAMPLE 1

A mixture of semicarbazide hydrochloride (1.0 mole; 111.53 g), 88 percent formic acid (2.5 moles; 130.77 g) and sulfuric acid (0.1 mole; 10.33 g; 95 percent $H_2SO_4$) was heated to 111°-115° C. for four hours. The formic acid/$H_2O$ azeotrope formed was distilled (84 ml), $H_2O$ (40 ml) added and stripping continued (25 ml).

The residue was chilled to 0° C., filtered, washed with cold $H_2O$ (0° C./40 ml); and vacuum dried to give 71.52 g (0.841 mole; 84.1 percent yield) of 1,2,4-triazol-5-one, m.p. 210°-217° C. The chloride ion concentration, as determined by ion chromatography, was 1665 ppm.

Recrystallization of 18.3 g of the crude product in $H_2O$ (32 ml/90° C.) gave 14.9 g of 1,2,4-triazol-5-one, m.p. 220°-231° C. The chloride ion concentration was reduced to 97 ppm. Overall yield of recrystallized 1,2,4-triazol-5-one was 67.7 percent.

Comparative Example A

The process of EXAMPLE 1 was repeated exactly with the single exception that the sulfuric acid catalyst was omitted. Recrystallization of 18.0 g of the crude product gave 15.4 g of 1,2,4-triazol-5-one having a chloride ion content of 347 ppm. Overall yield of recrystallized 1,2,4-triazol-5-one was 74.2 percent.

EXAMPLE 2

Semicarbazide (as the free base) was isolated by cooling methanol solutions prepared as described in U.S. Pat. No. 4,482,738, filtering and vacuum-drying, m.p. 92°-94° C.

A mixture consisting of semicarbazide (1.0 mole; 75.07 g), formic acid (2.5 moles; 127.9 g; 90 percent assay) and sulfuric acid (0.1 mole; 9.8 g; 98 percent $H_2SO_4$ concentration) was heated at 103°-117°20 C. for four hours. The formic acid-water azeotrope was stripped (20 ml), $H_2O$ (40 ml) added and stripping resumed (80 ml). The residue was cooled to 0° C., filtered, washed with 40 ml $H_2O$ (0° C.) and vacuum dried to give 43.3 g (0.509 mole; 50.9 percent yield) of 1,2,4-triazol-5-one, m.p. 202°-218° C.

Recrystallization of the crude product (10 g) in $H_2O$ (90 ml) at 50° C. gave 4.2 g of purified 1,2,4-triazol-5-one, m.p. 237.5°-238.5° C., with a chloride ion content of 7.9 ppm. $C^{13}$ NMR confirmed the Structure of the desired product.

EXAMPLE 3

Sulfuric acid (0.5 mole; 50.0 g; 98 percent) was added to 90 percent formic acid (2.5 moles; 127.9 g) followed by the addition of semicarbazide (1.0 mole; 75.07 g) and the contents heated at 112°–119° C. for 4.25 hours. The amount of $H_2SO_4$ used was sufficient to catalyze the reaction and to generate semicarbazide bisulfate in situ. A formic acid-$H_2O$ azeotrope was stripped (67 ml), $H_2O$ (40 ml) added and stripping continued (33 ml). The residue was cooled to 0° C., filtered, washed with cold water (50 ml) and vacuum dried. The mother liquor was refrigerated and additional product was collected. The combined yield of crude 1,2,4-triazol-5-one product was 94.9 percent (80.16 g; 0.949 mole).

The crude product (10 g) was recrystallized in $H_2O$ (90 ml) at 35°–40° C. to give 4.96 g of 1,2,4-triazol-5-one, m.p. 234°–239° C. The chloride ion concentration as determined by ion chromatography was 13.5 ppm.

EXAMPLE 4

Semicarbazide (1.0 mole; 75.0 g), trimethyl orthoformate (2.5 moles; 265.3 g) and sulfuric acid (0.1 mole; 10.33 g; 95 percent) were heated at 60° C. for six hours. The reaction mixture was cooled to −10° C., filtered, washed with methanol (40 ml/0° C.), and vacuum-dried to give 69.1 g (0.813 mole; 81 percent yield) of 1,2,4-triazol-5-one, m.p. 230°–234° C.

A portion of the crude product (2.93 g) was purified by solubilization in methanol (100 ml). Filtration of trace insolubles, concentration of the filtrate and cooling gave a white product, weight 2.39 g (after vacuum-drying), m.p. 235.5°–237° C. The chloride ion content was <50 ppm. $C^{13}$NMR confirmed the product to be solely 1,2,4-triazol-5-one and devoid of other impurities.

Overall yield of the recrystallized product was 66.3 percent.

What is claimed is:

1. A process for producing 1,2,4-triazol-5-one which comprises reacting semicarbazide or a salt thereof with a formic acid formulating agent selected from the group consisting of formic acid, formic acid esters of a lower alcohol having 1 to 6 carbon atoms, and orthoformic acid esters of a lower alcohol having 1 to 6 carbon atoms in the presence of a catalytic amount of a sulfur-oxygen containing acid selected from the group consisting of sulfuric acid, oleum and sulfurous acid.

2. The process of claim 1 in which the catalytic amount of the sulfur-oxygen containing acid is a molar ratio to the semicarbazide compound of from about 0.05:1 to about 1:1.

3. The process of claim 1 in which the sulfur-oxygen containing acid is sulfuric acid or oleum.

4. The process of claim 3 in which the molar ratio of the sulfur-oxygen containing acid to the semicarbazide compound is from about 0.1:1 to about 0.5:1.

5. The process of claim 4 in which the formic acid formulating agent is formic acid.

6. The process of claim 4 in which the semicarbazide compound is semicarbazide hydrochloride.

7. The process of claim 4 in which the semicarbazide compound is semicarbazide.

8. The process of claim 4 in which the formic acid formulating agent is an orthoformic acid ester of an alcohol having 1 to about 3 carbon atoms.

9. The process of claim 4 in which the formic acid formulating agent is a formic acid ester of an alcohol having 1 to about 3 carbon atoms.

10. A process for producing 1,2,4-triazol-5-one by reacting semicarbazide with a formic acid ester or orthoformic acid ester of a lower alcohol having 1 to about 6 carbon atoms, in the presence of a catalytic amount of sulfuric acid.

* * * * *